United States Patent [19]

Brown et al.

[11] Patent Number: 5,698,752

[45] Date of Patent: Dec. 16, 1997

[54] SELECTIVE HYDROGENATION PROCESS

[75] Inventors: Scott H. Brown; James B. Kimble, both of Bartlesville, Okla.; Stan A. Zisman, Lake Jackson, Tex.

[73] Assignee: Phillips Petroleum Company, Bartlesville, Okla.

[21] Appl. No.: 685,120

[22] Filed: Jul. 23, 1996

Related U.S. Application Data

[62] Division of Ser. No. 424,733, Apr. 19, 1995, Pat. No. 5,587,348.

[51] Int. Cl.$^6$ .............. C07C 5/02; C07C 5/03; C07C 5/05; C07C 5/08
[52] U.S. Cl. .......... 585/260; 585/258; 585/259; 585/261; 585/262; 585/271; 585/273; 585/275; 585/277; 585/500; 585/601
[58] Field of Search ............. 585/258, 259, 585/260, 261, 262, 271, 273, 275, 277, 500, 601

[56] References Cited

U.S. PATENT DOCUMENTS

| | | |
|---|---|---|
| 3,325,556 | 6/1967 | Rosset. |
| 4,009,126 | 2/1977 | McFarland. |
| 4,404,124 | 9/1983 | Johnson et al. |
| 4,644,088 | 2/1987 | McFarland ............... 585/658 |
| 4,658,080 | 4/1987 | McFarland ............... 585/658 |
| 5,032,565 | 7/1991 | Berrebi ................... 502/331 |
| 5,059,731 | 10/1991 | Berrebi ................... 585/259 |
| 5,068,477 | 11/1991 | Berrebi ................... 585/274 |
| 5,488,024 | 1/1996 | Cheung et al. ........... 502/325 |
| 5,489,565 | 2/1996 | Cheung et al. ........... 502/325 |
| 5,510,550 | 4/1996 | Cheung et al. ........... 585/259 |
| 5,583,274 | 12/1996 | Cheung et al. ........... 585/261 |
| 5,585,318 | 12/1996 | Johnson et al. .......... 502/330 |

OTHER PUBLICATIONS

Yeung H. Park et al., "Promotional Effects of Potassium on Pd/Al$_2$O$_3$ Selective Hydrogenation Catalysts"; Ind. Eng. Chem. Res. 1992, 31, p. 469–474 no month available.

*Primary Examiner*—Elizabeth D. Wood
*Attorney, Agent, or Firm*—Lucas K. Shay & Karl K. Brandes

[57] ABSTRACT

A selective hydrogenation of an alkyne in an olefin-containing fluid is provided which comprises contacting the fluid and hydrogen gas with a catalyst in the presence of at least one sulfur compound, under reaction conditions effective to produce at least one alkene wherein the catalyst comprises at least one alkali metal, fluorine and an inorganic support material.

23 Claims, No Drawings

SELECTIVE HYDROGENATION PROCESS

This application is a division of U.S. patent application Ser. No. 08/424,733, filed Apr. 19, 1995, now U.S. Pat. No. 5,587,348.

BACKGROUND OF THE INVENTION

In one aspect, this invention relates to a supported, alkali metal fluoride-promoted palladium catalyst composition. In another aspect, this invention relates to a method of preparing this catalyst composition. In a further aspect, this invention relates to a process for selectively hydrogenating alkynes to alkenes, particularly acetylene to ethylene, in the presence of sulfur impurities employing the above-described catalyst composition.

The selective hydrogenation of alkynes, which frequently are present in small amounts in alkene-containing streams (e.g., acetylene contained in ethylene streams from thermal alkane crackers), is commercially carried out in the presence of supported palladium catalysts. In the case of the selective hydrogenation of acetylene to ethylene, preferably an alumina-supported palladium/silver catalyst in accordance with the disclosure in U.S. Pat. No. 4,404,124 and its division, U.S. Pat. No. 4,484,015, is used. The operating temperature for this hydrogenation process is selected such that essentially all acetylene is hydrogenated to ethylene (and thus removed from the feed stream) while only an insignificant amount of ethylene is hydrogenated to ethane (to minimize ethylene losses and to avoid a "runaway" reaction which is difficult to control, as has been pointed out in the above-identified patents).

It is generally known by those skilled in the art that sulfur impurities (such as $H_2S$, COS, $CS_2$, mercaptans and organic sulfides and polysulfides) when present in alkyne-containing feeds can poison and deactivate these palladium-containing catalysts. The present invention is directed to an improved palladium-containing catalyst which is used for selectively hydrogenating alkynes to alkene, in particular of acetylene to ethylene, in the presence of sulfur-containing impurities.

SUMMARY OF THE INVENTION

It is an object of this invention to provide an improved, more sulfur-resistant supported Pd-containing catalyst. It is another object of this invention to prepare this improved catalyst. It is a further object of this invention to use this catalyst in the selective hydrogenation of alkynes to alkenes, particularly acetylene to ethylene, in the presence of sulfur impurities. Other objects and advantages will be apparent from the detailed description and appended claims.

In accordance with this invention, a catalyst composition comprises palladium, at least one chemically bound alkali metal, chemically bound fluorine, and an inorganic support material, wherein the atomic ratio of fluorine to said at least one alkali metal is in the range of about 1.3:1 to about 4:1. Preferably, the alkali metal is potassium, the at least one fluorine compound is ammonium fluoride, and the support material is alumina. More preferably, the above catalyst composition also comprises silver.

In a preferred embodiment, the above-described catalyst composition (containing F and at least one alkali metal at an atomic ratio of about 1.3:1 to about 4:1) is prepared by a method comprising contacting a solid, composition comprising palladium and an inorganic support material (preferably alumina) with at least one dissolved alkali metal compound (preferably at least one potassium compound) and with at least one fluorine compound selected from the group consisting of hydrogen fluoride (HF), ammonium fluoride ($NH_4F$) and ammonium bifluoride ($NH_4HF_2$). Any water-soluble alkali metal compound can be used, such as hydroxide, bicarbonate, carbonate, nitrate, bisulfate, fluoride and the like, preferably hydroxide or fluoride. These compounds are preferably dissolved in water. Preferably, the contacting with the dissolved potassium compound (more preferably KOH) is carried out in the presence of a "wet-reducing" compound (more preferably an aqueous solution of formaldehyde or dextrose). Preferably, the solid supported palladium-containing starting composition also contains silver (as Ag metal and/or Ag oxide).

Also in accordance with this invention, a process for selectively hydrogenating (with hydrogen gas) at least one alkyne containing 2–10 carbon atoms per molecule to at least one alkene containing 2–10 carbon atoms per molecule in the presence of at least one sulfur compound (as impurity) is carried out with the above-described catalyst composition (containing F and at least one alkali metal at an atomic ratio of about 1.3:1 to about 4:1). Preferably, the at least one alkyne is acetylene ($C_2H_2$). The at least one sulfur compound is generally selected from the group consisting of hydrogen sulfide, carbonyl sulfide (COS), carbon disulfide, alkyl mercaptans, dialkyl sulfides, dialkyl disulfides and dialkyl polysulfides, wherein each alkyl group can contain 1–10 carbon atoms, and mixtures thereof.

DETAILED DESCRIPTION OF THE INVENTION

The catalyst composition of this invention comprises (a) palladium (as metal and/or at least one Pd compound), (b) at least one alkali metal (preferably potassium, generally chemically bound as hydroxide or oxide or fluoride), (c) chemically bound fluorine (at least one non-alkali metal fluoride, or a mixture of at least one alkali metal fluoride and at least one non-alkali metal fluoride), and (d) an inorganic support material (preferably selected from the group consisting of alumina, titania, zirconia, and mixtures thereof). The presently more preferred support material is alumina, most preferably alpha-alumina. Preferably, the catalyst also contains silver (as Ag metal and/or at least one Ag compound).

This catalyst generally contains about 0.01–1 (preferably about 0.01–0.2) weight-% palladium, about 0.05–5 (preferably about 0.1–1) weight-% alkali metal (preferably K, Rb, Cs; more preferably K), and about 0.03–10 (preferably about 0.2–1) weight-% fluorine (chemically bound as fluoride), whereto all recited weight percentages are on elemental basis. The atomic ratio of F to alkali metal(s) is about 1.3:1 to about 4:1 (preferably about 1.4:1 to about 3:1). The preferred alkali metal to Pd weight ratio is about 0.05:1 to about 500:1, more preferably about 0.2:1 to about 100:1. Preferably, about 0.01–10 (more preferably about 0.02–2) weight-% silver is also present in the catalyst. Preferably, the Ag:Pd weight ratio in the catalyst is about 2:1 to about 10:1. Particles of this catalyst generally have a size of about 1–10 mm (preferably about 2–6 mm) and can have any suitable shape (preferably spherical or cylindrical). Generally, the surface area of this catalyst (determined by the BET method employing $N_2$) is about 1–100 $m^2/g$.

The above-described hydrogenation catalyst can be prepared by any suitable, effective method. The at least one alkali metal compound can be incorporated (e.g., by impregnation or spraying) into the support material before it is impregnated with a suitable Pd compound, and preferably also with a suitable Ag compound. Or the at least one alkali metal compound can be incorporated (e.g., by impregnation or spraying) into the catalyst simultaneously with or after the impregnation with a suitable Pd compound. When silver is also present in the catalyst composition, the at least one alkali metal compound can be incorporated between the Pd and Ag impregnation steps or after the impregnation with Pd and Ag compounds. In the presently preferred catalyst preparation, a supported Pd/Ag catalyst material (more preferably the Pd/Ag/Al$_2$O$_3$ catalyst obtained by the method described in U.S. Pat. Nos. 4,404,124 and 4,484,015) is impregnated with an aqueous solution of at least one alkali metal hydroxide and/or at least one alkali metal fluoride (preferably KOH and/or KF), followed by drying (generally at about 50°–150° C.) and calcining (preferably in air at a temperature of about 300°–700° C., more preferably about 400°–600° C., preferably for about 0.2–20 hours, more preferably about 1–6 hours). It is presently also preferred to have at least one "wet-reducing" agent (i.e., one or more than one dissolved reducing agent) present during the contacting of the supported Pd/Ag catalyst with at least one alkali metal hydroxide and/or at least one alkali metal fluoride. Non-limiting examples of such "wet-reducing" agents are: hydrazine, at least one alkali metal borohydride, at least one aldehyde containing 1–6 carbon atoms per molecule such as formaldehyde, at least one ketone containing 1–6 carbon atoms per molecule, at least one carboxylic acid containing 1–6 carbon atoms per molecule such as formic acid or ascorbic acid, at least one reducing sugar containing an aldehyde or alpha-hydroxyketone group such as dextrose, and the like.

The non-alkali metal fluoride (preferably HF or NH$_4$F or NH$_4$HF$_2$ or mixtures thereof, more preferably NH$_4$F) can be incorporated into said catalyst in any suitable manner. The non-alkali metal fluoride (preferably NH$_4$F) can be incorporated together with Pd and alkali metal compounds (and preferably a suitable Ag compound). Or, preferably, the non-alkali metal fluoride can be incorporated after the impregnation of the solid support material with the Pd and at least one alkali metal compound (and preferably also a suitable Ag compound). After the incorporation of Pd, alkali metal, fluoride (and preferably also Ag) compounds into the support material has been completed (as described above), the thus-obtained material is dried (generally at about 50°–150° C., for about 0.2–20 hours) and then calcined (generally at a temperature of about 300°–700° C., for about 0.2–20 hours). Optionally, the calcined material can then be reduced with hydrogen gas (preferably at about 30°–100° C., for about 0.5–20 hours), so as to reduce oxides of Pd and of Ag (if present) to the corresponding metal(s).

The selective hydrogenation process of this invention is carried out by contacting (a) a feed which comprises at least one C$_2$–C$_{10}$ alkyne (preferably a C$_2$–C$_{10}$ alkene stream containing said at least one alkyne as an impurity, generally at a level of about 1 ppm by weight to about 50,000 ppm by weight alkyne) and at least one sulfur compound (as an impurity) and (b) hydrogen gas with (c) the effective alkyne hydrogenation catalyst composition of this invention (described above). Preferred feed alkynes include acetylene, propyne, butyne-1, butyne-2 and mixtures thereof. Particularly preferred is acetylene. These alkynes are primarily hydrogenated to the corresponding alkenes, i.e., acetylene is primarily hydrogenated to ethylene, propyne is primarily hydrogenated to propylene, and the butynes are primarily hydrogenated to the corresponding butenes (butene-1, butene-2). In order to best attain substantially complete removal of the alkyne(s), there should be at least one mole of hydrogen for each mole of alkyne present. Fluids (a) and (b) are generally premixed before their contact with the catalyst composition (c).

Suitable sulfur compounds which are present as impurities in the feed include (but are not limited to) hydrogen sulfide, carbonyl sulfide (COS), carbon disulfide (CS$_2$), mercaptans (RSH), organic sulfides (R—S—R), organic disulfides (R—S—S—R), organic polysulfides (R—S$_x$—R) and the like, and mixtures thereof, wherein each R can be an alkyl or cycloalkyl or aryl group containing 1–10 carbon atoms and x is a whole number which can range from 3 to 10. It is within the scope of this invention to have the sulfur impurities intermittently (i.e., not always but occasionally) present in the feed, e.g., when occasional upstream malfunctioning of an ethane cracker or of a guard bed occurs. It is also within the scope of this invention to have additional compounds (such as methane, ethane, propane, butane, carbon monoxide, water, alcohols, ethers, ketones, carboxylic acids, esters and other oxygenated compounds) present in the feed gas, as long as they do not significantly interfere with the selective hydrogenation of alkyne(s) to alkene(s). Generally, the sulfur compounds are present in the feed gas in trace amounts, at a level of less than about 1 weight percent sulfur on an elemental basis, and preferably at a level of about 1 ppb to about 1,000 ppm by weight sulfur (ppb=parts by weight of S per billion parts by weight of total feed; ppm=parts by weight of S per million parts by weight of total feed).

The temperature necessary for the selective hydrogenation of alkyne(s) to alkene(s) depends largely upon the activity and selectivity of the catalysts, the amounts of sulfur impurities in the feed, and the desired extent of alkyne removal. Generally, a reaction temperature in the range of about 0° C. to about 250° C. is employed. Preferably, the reaction temperature is about 30°–150° C. Any suitable reaction pressure can be employed. Generally, the total pressure is in the range of about 100 to about 1,000 pounds per square inch gauge (psig). The hydrocarbon feed can be liquid or gaseous at the reaction conditions. If the feed is introduced into the reaction zone as a gas, the gas hourly space velocity (GHSV) will be in the range of about 1,000 to about 10,000 m$^3$ of feed per m$^3$ of catalyst per hour, more preferably about 2,000 to about 8,000 m$^3$/m$^3$/hour. The GHSV of the hydrogen gas stream is chosen so as to provide a molar ratio of H$_2$ to said at least an alkyne in the range of about 0.5:1 to about 200:1, preferably about 1:1 to about 100:1.

Regeneration of the alkyne hydrogenation catalyst composition of this invention, after it has been partially deactivated in an alkyne hydrogenation process, can be accomplished by heating the catalyst composition in air (at a temperature which preferably does not exceed about 700° C.) so as to burn off any sulfur compounds, organic matter and/or char that may have accumulated on the catalyst composition. Optionally, the oxidatively regenerated composition is reduced with H$_2$ or a suitable hydrocarbon (as has been described above) before its redeployment in the selective alkyne hydrogenation of this invention.

The following examples are presented to further illustrate the invention and are not to be construed as unduly limiting the scope of this invention.

EXAMPLE I

This example illustrates the preparation of Pd/Ag/Al$_2$O$_3$ catalysts which had been treated with KOH and NH$_4$F.

Catalyst A1 (Control) was a fresh, commercial Pd/Al/Al$_2$O$_3$ catalyst containing 0.02 weight-% Pd, about 0.07 weight-% Ag and about 99 weight-% alumina and having a surface area of about 3–5 m²/g (measured by the BET/N₂ method). This catalyst (product designation "G-83C") had been prepared by United Catalysts, Inc. (UCI), Louisville, Ky., substantially in accordance with the procedure described in U.S. Pat. No. 4,404,124 (column 4, lines 32–48).

Catalyst A2 (Control) was a "G-83C" Pd/Al/Al₂O₃ catalyst (described above) which had been used in a commercial acetylene hydrogenation process and had then be regenerated by heating it in air to a temperature of about 1000° F. within a time period of about 3 hours, calcining it in air at that temperature for about 4 hours (until the carbon content in the catalyst was less than about 0.2 weight-%), and cooling it to room temperature.

Catalyst B1 (Control) was commercially produced essentially in accordance with the following general recipe: 300 lb of Catalyst A1 tablets (size: 3/16"×3/16") were contacted with an aqueous solution which contained 6 lb of dextrose (as reducing agent), 9.6 lb of 88 weight-% KOH pellets and 300 lb of H₂O. The mixture was kept, with occasional stirring, at room temperature for about one hour. Excess liquid was decanted, and the "wet-reduced" tablets were then calcined in air at about 538° C. for about 2 hours. Catalyst B1 contained about 0.5 weight-% K, about 0.02 weight-% Pd and about 0.07 weight-% Ag.

Catalyst B2 (Control) was prepared essentially according to the procedure for Catalyst B1 except that Catalyst A2 tablets were used as the starting material. Catalyst B2 also contained about 0.5 weight-% K, about 0.02 weight-% Pd and about 0.07 weight-% Ag.

Catalyst C (Control) was prepared by incipient wetness impregnation of 25.0 grams of Catalyst B2 with a solution of 0.059 gram of NH₄F in 6.0 grams of distilled water by adding the aqueous solution dropwise to the catalyst with stirring, followed by drying the thus-impregnated catalyst at about 125° C. for about 2 hours and calcining it in air at about 538° C. for about 2 hours. The fluorine content of Catalyst C was about 0.12 weight-% F, and the atomic ratio of F:K was about 0.5:1.

Catalyst D (Control) was prepared in accordance with the procedure for Catalyst C except that the amount of dissolved NH₄F was 0.118 gram. The fluorine content of Catalyst D was about 0.25 weight-% F, and the atomic ratio of F:K was about 1:1.

Catalyst E (Invention) was prepared in accordance with the procedure for Catalyst C except that the amount of dissolved NH₄F was about 0.237 gram. The fluorine content of Catalyst E was about 0.49 weight-% F, and the atomic ratio of F:K was about 2:1.

Catalyst F (Invention) was prepared in accordance with the procedure for Catalyst C except that the amount of dissolved NH₄F was 0.474 gram. The fluorine content of Catalyst F was about 0.97 weight-% F, and the F:K atomic ratio was about 4:1.

Catalyst G (Invention) was prepared essentially in accordance with the procedure for Catalyst C except that 75 grams of Catalyst B1 (in lieu of Catalyst B2) and a solution of 0.70 gram of NH₄F in 17.75 grams of distilled water were used. The fluorine content of Catalyst G was about 0.48 weight-% F, and the atomic ratio of F:K was about 2:1.

EXAMPLE II

This example illustrates the performance of the catalysts described in Example I in the selective hydrogenation of acetylene to ethylene in the presence of sulfur impurities.

About 20 cc (about 23 g) of each of the above-described catalysts was placed in a stainless steel reactor tube having a 0.5 inch inner diameter and a length of about 18 inches. Each catalyst was treated with flowing hydrogen gas under a pressure of 200 psig, at a temperature of about 100°–110° F., for about 0.5 hour. Thereafter, a hydrocarbon-containing feed gas containing 3.2 weight-% hydrogen, 29.7 weight-% methane, 0.02 weight-% ethane, about 66.7 weight-% ethylene, 0.34 weight-% acetylene and 0.05 weight-% carbon monoxide was introduced into the reactor tube at a rate of about 900 cc/minute. The reactor temperature was gradually increased to the desired reaction temperature, and samples of the formed product were analyzed at various time intervals by means of a gas chromatograph.

The following test results are summarized in Table I: $T_1$, which is the "cleanup" temperature at which acetylene substantially hydrogenated to ethylene so as to obtain a product containing less than about 20 ppm (ppm=parts per million parts by weight) of acetylene; $T_2$, which is the "runaway" temperature at which a significant portion of ethylene (about 4.5%) is converted to ethane (exothermic "runaway" reaction); and the amount of ethane formed (by ethylene hydrogenation) at temperature $T_1$.

TABLE I

| Catalyst | F:K Atomic Ratio | $T_1$ (°F.) | $T_2$(°F.) | $T_2 - T_1$ | ppm Ethane Formed at $T_1$ |
|---|---|---|---|---|---|
| B2 (Control) | 0 | 141 | 241 | 100 | ~400 |
| C (Control) | 0.5:1 | 161 | 245 | 84 | ~1000 |
| D (Control) | 1:1 | 152 | 235 | 83 | ~1100 |
| E (Invention) | 2:1 | 134 | 210 | 76 | ~900 |
| F (Invention) | 4:1 | 131 | 199 | 68 | ~900 |
| G (Invention) | 2:1 | 138 | 206 | 68 | ~1000 |

In order to more realistically predict the performance of the above-described catalysts in acetylene hydrogenation operations employing feeds that can contain catalyst poisons, the resistance of the above-described catalyst to a sulfur poison was determined by exposing each catalyst at a temperature of about 10°–20° F. above its "cleanup" temperature ($T_1$, see Table I) to a dose of 100 cc nitrogen gas containing 1000 ppm COS (carbonyl sulfide) which was injected into the reactor. The gradual recovery of the acetylene hydrogenation activity of the catalysts after the exposure to COS was determined by measuring the mount of unconverted acetylene in the product at various time intervals after the COS exposure. Test results (for two successive COS injections) are summarized in Table II.

TABLE II

| Catalyst | Reaction Temp. (°F.) | Time (Minutes) After COS Injection | Unconverted Acetylene (ppm) in Product |
|---|---|---|---|
| B1 (Control)[1] | 160 | 0 | 1 |
|  | 162 | 10 | 71 |
|  | 161 | 45 | 29 |
|  | 159 | 80 | 19 |
|  | 160 | 145 | 15 |
| B1 (Control)[2] | 160 | 10 | 223 |
|  | 160 | 52 | 111 |
|  | 160 | 81 | 83 |
|  | 160 | 115 | 70 |
|  | 160 | 150 | 63 |
| B2 (Control)[1] | 165 | 0 | 3 |
|  | 165 | 10 | 80 |
|  | 165 | 41 | 39 |

TABLE II-continued

| Catalyst | Reaction Temp. (°F.) | Time (Minutes) After COS Injection | Unconverted Acetylene (ppm) in Product |
|---|---|---|---|
|  | 165 | 73 | 26 |
|  | 165 | 105 | 22 |
|  | 165 | 137 | 16 |
| B2 (Control)[2] | 164 | 10 | 155 |
|  | 164 | 42 | 81 |
|  | 164 | 73 | 58 |
|  | 164 | 103 | 50 |
|  | 164 | 167 | 40 |
| C (Control)[1] | 178 | 0 | 0 |
|  | 178 | 10 | 43 |
|  | 177 | 35 | 15 |
|  | 176 | 70 | 8 |
| C (Control)[2] | 177 | 10 | 98 |
|  | 176 | 39 | 36 |
|  | 175 | 67 | 26 |
|  | 177 | 104 | 20 |
| D (Control)[1] | 162 | 0 | 0 |
|  | 161 | 10 | 130 |
|  | 162 | 42 | 21 |
|  | 162 | 73 | 14 |
|  | 163 | 109 | 11 |
| D (Control)[2] | 162 | 10 | 219 |
|  | 161 | 43 | 69 |
|  | 161 | 74 | 45 |
|  | 161 | 105 | 33 |
| E (Invention)[1] | 152 | 0 | 0 |
|  | 151 | 12 | 13 |
|  | 151 | 53 | 0 |
| E (Invention)[2] | 152 | 0 | 0 |
|  | 150 | 11 | 57 |
|  | 151 | 49 | 6 |
|  | 151 | 118 | 3 |
| F (Invention)[1] | 148 | 0 | 0 |
|  | 146 | 10 | 41 |
|  | 147 | 42 | 3 |
|  | 147 | 74 | 3 |
| F (Invention)[2] | 147 | 0 | 2 |
|  | 145 | 10 | 329 |
|  | 146 | 41 | 16 |
|  | 146 | 78 | 11 |
| G (Invention)[1] | 150 | 0 | 0 |
|  | 149 | 12 | 133 |
|  | 149 | 42 | 7 |
|  | 149 | 75 | 3 |
| G (Invention)[2] | 150 | 0 | 3 |
|  | 150 | 12 | 159 |
|  | 150 | 52 | 7 |
|  | 150 | 81 | 3 |

[1]first COS injection.
[2]second COS injection

Test data in Table II clearly show that invention catalysts E, F and G (having an atomic F:K ratio of 2:1 to 4:1 ) recovered their acetylene hydrogenation activity more rapidly than the control catalysts (having an atomic K:F ratio of 0 to 1:1). Thus, it is concluded that the deactivation of the invention catalysts caused by sulfur impurities in hydrocarbon feeds for commercial acetylene removal processes will also be considerably lower (as compared with corresponding catalysts containing either no fluoride or fluoride at a F to alkali metal ratio of up to the stoichiometric ratio of 1:1). An additional test (not described herein in detail) indicated that a catalyst which had an atomic K:F ratio of 1.6:1 was essentially as effective as the above-described, particularly preferred catalysts having a 2:1 ratio (Catalysts E and G)

Reasonable variations and modifications which will be apparent to those skilled in the art, can be made within the scope of the disclosure and appended claims without departing from the scope of this invention.

That which is claimed:

1. A selective hydrogenation process which comprises contacting (a) a feed comprising at least one alkyne containing 2–10 carbon atoms per molecule and (b) hydrogen gas with (c) an effective catalyst in the presence of at least one sulfur compound, under reaction conditions effective to produce at least one alkene containing 2–10 carbon atoms per molecule, wherein said catalyst comprises about 0.01–1 weight-% palladium, about 0.05–5 weight-% of at least one alkali metal, about 0.03–10 weight-% fluorine and an inorganic support material, and wherein the atomic ratio of fluorine to said at least one alkali metal in said catalyst is in the range of about 1.3:1 to about 4:1.

2. A process in accordance with claim 1, wherein said at least one alkali metal is selected from the group consisting of potassium, rubidium and cesium, and said inorganic support material is selected from the group consisting of alumina, titania, zirconia and mixtures thereof.

3. A process in accordance with claim 2, wherein said at least one alkali metal is potassium, said inorganic support material is alumina, and the weight ratio of potassium to palladium is in the range of about 0.05:1 to about 500:1.

4. A process in accordance with claim 2, wherein said catalyst has been prepared by a method which comprises contacting a solid composition comprising palladium and said inorganic support material with (i) at least one dissolved alkali metal compound selected from the group consisting of hydroxides, bicarbonates, carbonates, nitrates, bisulfates and fluorides and with (ii) at least one dissolved fluorine compound selected from the group consisting of hydrogen fluoride, ammonium fluoride and ammonium bifluoride.

5. A process in accordance with claim 2, wherein said at least one sulfur compound is selected from the group consisting of hydrogen sulfide, carbonyl sulfide, carbon disulfide, mercaptans having the general formula of RSH, organic sulfides having general formula of R—S—R, organic disulfides having the general formula of R—S—S—R, organic polysulfides having the general formula of R—S$_x$—R, and mixtures thereof, wherein each R can be an alkyl or cycloalkyl or aryl group containing 1–10 carbon atoms and x is a whole number ranging from 3 to 10.

6. A process in accordance with claim 5, wherein said at least one alkyne is acetylene, said at least one alkene is ethylene, and said at least one sulfur compound is selected from the group consisting of hydrogen sulfide, carbonyl sulfide, carbon disulfide, alkyl mercaptans, dialkyl sulfides, dialkyl disulfides, dialkyl polysulfides and mixtures thereof.

7. A process in accordance with claim 6, wherein said at least one sulfur compound is present in said feed at a level of about 1 ppb to about 1,000 ppm sulfur.

8. A process in accordance with claim 2, wherein said contacting of (a) and (b) with (c) is carried out at a reaction temperature of about 0°–250° C., a total pressure of about 100–1,000 psig, and a molar ratio of hydrogen to acetylene of about 0.5:1 to about 200:1.

9. A process in accordance with claim 1, wherein said catalyst additionally comprises about 0.01–10 weight-% silver.

10. A process in accordance with claim 9, wherein said at least one alkali metal is selected from the group consisting of potassium, rubidium and cesium, and said inorganic support material is selected from the group consisting of alumina, titania, zirconia and mixtures thereof.

11. A process in accordance with claim 10, wherein said at least one alkali metal is potassium, said inorganic support material is alumina, and the weight ratio of potassium to palladium is in the range of about 0.05:1 to about 500:1.

12. A process in accordance with claim 10, wherein the weight ratio of silver to palladium in said catalyst is about 2:1 to about 10:1.

13. A process in accordance with claim 10, wherein said catalyst has been prepared by a method which comprises contacting a solid composition comprising palladium, silver and said support material with (i) at least one dissolved alkali metal compound selected from the group consisting of hydroxides, bicarbonates, carbonates, nitrates, bisulfates and fluorides and with (ii) at least one dissolved fluorine compound selected from the group consisting of hydrogen fluoride, ammonium fluoride and ammonium bifluoride.

14. A process in accordance with claim 10, wherein said catalyst has been prepared by a method which comprises impregnating a solid material comprising palladium, silver and said inorganic support material with: (1) an aqueous solution comprising ($\alpha$) at least one reducing agent selected from the group consisting of hydrazine, alkali metal borohydrides, aldehydes containing 1–6 carbon atoms per molecule, ketones containing 1–6 carbon atoms per molecule, carboxylic acids containing 1–6 carbon atoms per molecule, reducing sugars containing an aldehyde group, and reducing sugars containing an alpha-hydroxyketone group and ($\beta$) at least one dissolved alkali metal compound selected from the group consisting of hydroxides and fluorides, and thereafter with (2) at least one dissolved fluorine compound selected from the group consisting of hydrogen, fluoride, ammonium fluoride and ammonium bifluoride.

15. A process in accordance with claim 14, wherein said at least one reducing agent is selected from the group consisting of hydrazine, formaldehyde, formic acid, ascorbic acid and dextrose, and said at least one dissolved fluorine compound is ammonium fluoride.

16. A process in accordance with claim 10, wherein said at least one sulfur compound is selected from the group consisting of hydrogen sulfide, carbonyl sulfide, carbon disulfide, mercaptans having the general formula of RSH, organic sulfides having general formula of R—S—R, organic disulfides having the general formula of R—S—S—R, organic polysulfides having the general formula of R—S$_x$—R, and mixtures thereof, wherein each R can be an alkyl or cycloalkyl or aryl group containing 1–10 carbon atoms and x is a whole number ranging from 3 to 10.

17. A process in accordance with claim 16, wherein said at least one alkyne is acetylene, said at least one alkene is ethylene, and said at least one sulfur compound is selected from the group consisting of hydrogen sulfide, carbonyl sulfide, carbon disulfide, alkyl mercaptans, dialkyl sulfides, dialkyl disulfides, dialkyl polysulfides and mixtures thereof.

18. A process in accordance with claim 17, wherein said at least one sulfur compound is present in said feed at a level of about 1 ppb to about 1,000 ppm sulfur.

19. A process in accordance with claim 10, wherein said contacting of (a) and (b) with (c) is carried out at a reaction temperature of about 0°–250° C., a total pressure of about 100–1,000 psig, and a molar ratio of hydrogen to acetylene of about 0.5:1 to about 200:1.

20. A selective hydrogenation process which comprises contacting (a) a feed comprising at least one alkyne containing 2–10 carbon atoms per molecule and (b) hydrogen gas with (c) an effective catalyst in the presence of at least one sulfur compound under conditions effective to produce at least one alkene containing 2–10 carbon atoms per molecule wherein said catalyst comprises about 0.01–1 weight-% palladium, about 0.05–5 weight-% of at least one alkali metal, about 0.03–10 weight-% fluorine and an inorganic support material, and the atomic ratio of fluorine to said at least one alkali metal in said catalyst is in the range of about 1.3:1 to about 4:1;

said at least one alkali metal is selected from the group consisting of potassium, rubidium and cesium;

said inorganic support material is selected from the group consisting of alumina, titania, zirconia and mixtures thereof;

said at least one alkyne is acetylene;

said at least one alkene is ethylene; and said at least one sulfur compound is selected from the group consisting of hydrogen sulfide, carbonyl sulfide, carbon disulfide, alkyl mercaptans, dialkyl sulfides, dialkyl disulfides, dialkyl polysulfides and mixtures thereof.

21. A process in accordance with claim 20 wherein said at least one alkali metal is potassium, said inorganic support material is alumina, and the weight ratio of potassium to palladium is in the range of about 0.05:1 to about 500:1.

22. A process according to claim 21 wherein said catalyst further comprises about 0.01 to about 10 weight % silver.

23. A selective hydrogenation process which comprises contacting (a) an acetylene-containing feed and (b) hydrogen gas with (c) an effective catalyst in the presence of at least one sulfur compound under conditions effective to produce at least one alkene containing 2–10 carbon atoms per molecule wherein said catalyst comprises about 0.01 to about 1 weight-% palladium, about 0.01 to about 10 weight % silver, about 0.05 to about 5 weight-% of potassium, about 0.03 to about 10 weight-% fluorine and alumina, and the weight ratio of potassium to fluoride is in the range of about 1.3:1 to about 4:1; and said at least one sulfur compound is selected from the group consisting of hydrogen sulfide, carbonyl sulfide, carbon disulfide, alkyl mercaptans, dialkyl sulfides, dialkyl disulfides, dialkyl polysulfides and mixtures thereof and is present in said feed at levels of about 1 ppb to about 1,000 ppm.

* * * * *